(12) United States Patent
Tao et al.

(10) Patent No.: US 6,348,448 B1
(45) Date of Patent: *Feb. 19, 2002

(54) PEPTIDYL-2-AMINO-1-HYDROXYALKANESULFONIC ACID CYSTEINE PROTEASE INHIBITORS

(75) Inventors: Ming Tao, Maple Glen; Ron Bihovsky, Wynnewood, both of PA (US)

(73) Assignee: Cephalon, Inc., West Chester, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/060,491

(22) Filed: Apr. 15, 1998

Related U.S. Application Data

(60) Provisional application No. 60/044,676, filed on Apr. 18, 1997.

(51) Int. Cl.$^7$ .................................................. C07K 5/06
(52) U.S. Cl. ..................... 514/19; 514/17; 514/18; 530/330; 530/331; 530/345
(58) Field of Search ................... 514/18, 19, 17; 530/330, 331, 345

(56) References Cited

U.S. PATENT DOCUMENTS

| | | | |
|---|---|---|---|
| 4,596,789 | 6/1986 | Dutta et al. | 514/18 |
| 4,691,007 | 9/1987 | Dutta et al. | 530/331 |
| 4,883,863 | * 11/1989 | Abe | 530/331 |
| 5,304,470 | 4/1994 | Fischer et al. | 435/68.1 |
| 5,436,229 | 7/1995 | Ruterbories et al. | 514/18 |
| 5,847,201 | * 12/1998 | Wieczorek | 562/43 |

FOREIGN PATENT DOCUMENTS

WO 97/18190  5/1997  (WO).

OTHER PUBLICATIONS

Green, Lawrence R. J. org. Chem. 39(26), 3896–9, 1924.*
Kokeoh, Fritag C. J. Org. Chem. 40(11), 1632–6, 1975.*
Betterton, Eric A. Environ. Sci. Technol 22(1) 92–9, 1988.*
Lores, Agvin M. Chromotographic 37(7–8), 451–4, 1993.*
Nishizawa, R. et al., "Synthesis and Structure–Activity Relationships of Bestatin Analogues, Inhibitors of Aminopeptidase B", *J. Med. Chem.*, 1977, 20(4), 510–515.
Thompson, R.C., "[19] Peptide Aldehydes: Potent Inhibitors of Serince and Cysteine Proteases", *Meth. Enzymol.*, 1977, 46, 220–225.
Angelastro et al., "α–Diketone and α–Keto Ester Derivatives of N–Protected Amino Acids and Peptides as Novel Inhibitors of Cysteine and Serine Proteinases", *J. Med. Chem.*, 1990, 33, 11–13.
Harbeson et al., "Stereospecific Synthesis of Peptidyl α–Keto Amides as Inhibitors of Calpain", *J. Med. Chem.*, 1994, 37, 2918–2929.
Iqbal et al., "Subsite Requirements for Peptide Aldehyde Inhibitors of Human Calpain I", *Bioorg. Med. Chem. Lett.*, 1997, 7(5), 539–544.
Lehninger, *Biochemistry*, Second Edition, Worth Publishers, Inc., 1975, 73–75.
Meyer et al., "Biologically active monomeric and heterodimeric recombinant human calpain I produced using the baculovirus expression system", *Biochem J.*, 1996, 314, 511–519.

* cited by examiner

*Primary Examiner*—David Lukton
(74) *Attorney, Agent, or Firm*—Woodcock Washburn Kurtz Mackiewicz & Norris LLP

(57) ABSTRACT

The present invention is directed to novel peptidyl-2-amino-1-hydroxyalkanesulfonic acid inhibitors of cysteine proteases. Methods for the use of the protease inhibitors are also described.

33 Claims, No Drawings

PEPTIDYL-2-AMINO-1-HYDROXYALKANESULFONIC ACID CYSTEINE PROTEASE INHIBITORS

CROSS REFERENCE TO RELATED APPLICATIONS

This application claims benefit of U.S. Provisional Application Ser. No. 60/044,676, filed Apr. 18, 1997, the disclosure of which is hereby incorporated herein by reference in its entirety.

FIELD OF THE INVENTION

Peptidyl-2-amino-1-hydroxyalkanesulfonic acid inhibitors of cysteine proteases, methods for making these compounds, and methods for using the same are disclosed.

BACKGROUND OF THE INVENTION

Numerous cysteine proteases have been identified in human tissues. A "protease" is an enzyme which degrades proteins into smaller components (peptides). The term "cysteine protease" refers to proteases which are distinguished by presence therein of a cysteine residue which plays a critical role in the catalytic process. Mammalian systems, including humans, normally degrade and process proteins via a variety of enzymes including cysteine proteases. However, when present at elevated levels or when abnormally activated, cysteine proteases are involved in pathophysiological processes.

For example, calcium-activated neutral proteases ("calpains") comprise a family of intracellular cysteine proteases which are ubiquitously expressed in mammalian tissues. Two major calpains have been identified; calpain I and calpain II. While calpain II is the predominant form in many tissues, calpain I is thought to be the predominant form in pathological conditions of nerve tissues. The calpain family of cysteine proteases has been implicated in many diseases and disorders, including neurodegeneration, stroke, Alzheimer's disease, amyotrophy, motor neuron damage, spinal cord trauma, traumatic brain injury, acute central nervous system injury, muscular dystrophy, bone resorption, platelet aggregation, cataracts and inflammation. Calpain I has been implicated in excitatory amino-acid induced neurotoxicity disorders including ischemia, spinal cord trauma, traumatic brain injury, hypoglycemia and epilepsy.

The lysosomal cysteine protease cathepsin B has been implicated in arthritis, inflammation, myocardial infarction, tumor metastasis, and muscular dystrophy. Other lysosomal cysteine proteases include cathepsins C, H, L and S. Interleukin-1 β converting enzyme (ICE) is a cysteine protease which catalyzes the formation of interleukin-1β. Interleukin-1 β is an immunoregulatory protein implicated in inflammation, diabetes, septic shock, rheumatoid arthritis, and Alzheimer's disease. ICE has also been linked to apoptotic cell death of neurons which is implicated in a variety of neurodegenerative disorders including Parkinson's disease, ischemia, and amyotrophic lateral sclerosis (ALS).

Cysteine proteases are also produced by various pathogens. The cysteine protease clostripain is produced by *Clostridium histolyticum*. Other proteases are produced by *Trpanosoma cruzi*, malaria parasites *Plasmodium falciparum* and *P.vinckei* and *Streptococcus*. Viral cysteine proteases such as HAV C3 are essential for processing of picornavirus structural proteins and enzymes.

Given the link between cysteine proteases and various debilitating disorders, compounds which inhibit these proteases would be useful and would provide an advance in both research and clinical settings.

SUMMARY OF THE INVENTION

The present invention is directed to novel cysteine protease inhibitors which we refer to as peptidyl-2-amino-1-hydroxyalkanesulfonic acids. Exemplary compounds are represented by Formula I:

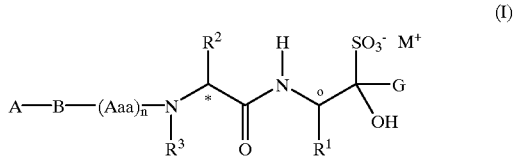

Constituent members and preferred embodiments are defined infra.

The compounds of the invention are useful for the inhibition of cysteine proteases. Beneficially, these compounds find utility in a variety of settings. For example, in a research arena, the subject compounds can be used as standards for screening in the discovery of agents for treating disorders associated with abnormal and/or aberrant activity of cysteine proteases. In a therapeutic arena, the compounds can be used to alleviate, mediate, reduce, and/or prevent disorders which are associated with abnormal and/or aberrant activity of cysteine proteases. One particular advantage of the subject compounds is that they have unexpectedly excellent solubility in aqueous media, approximately between 1 and 300 mg/mL. Thus, the compounds can be easily administered parenterally, for example intravenously, intrathecally or supradurally by bolus or infusion in the clinical or laboratory setting in media such as aqueous saline buffer.

Also disclosed are methodologies for making the peptidyl-2-amino-1-hydroxyalkanesulfonic acids. These and other features of the invention are set forth in more detail below.

DETAILED DESCRIPTION

Novel cysteine protease inhibitors have been discovered which are represented by Formula I:

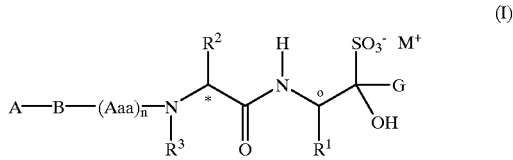

wherein:

* denotes the α-carbon of an α-amino acid residue having the L configuration;

o denotes a carbon having either stereochemical configuration, or a mixture thereof;

A is selected from the group consisting of lower alkyl, aryl having from 6 to about 14 carbons, heterocyclyl having from about 5 to about 14 ring atoms, heterocycloalkyl having from about 5 to about 14 ring atoms, aralkyl having from about 7 to about 15 carbons, and heteroarylalkyl, said alkyl, aryl, heterocyclyl, heterocycloalkyl, aralkyl and heteroarylalkyl groups being optionally substituted with J;

B is selected from the group consisting of C(=O), OC(=O), S(=O), S(=O)$_2$, and NR$^4$C(=O), where R$^4$ is H or lower alkyl;

each Aaa is independently an amino acid which optionally contains one or more blocking groups;

n is 0, 1, 2, or 3;

G is selected from the group consisting of H, C(=O)NR$^5$R$^6$, C(=O)OR$^5$, CF$_3$, CF$_2$R$^5$, P(=O) (R$^5$) (OR$^6$) and P(=O) (OR$^5$) (OR$^6$);

J is selected from the group consisting of halogen, lower alkyl, cycloalkyl, aryl, heteroaryl, heterocycloalkyl, aryl substituted with aralkyloxy, C(=O)OR$^7$, OC(=O)R$^7$, NR$^8$C(=O)OR$^7$, OR$^7$, CN, NO$_2$, NR$^7$R$^8$, N=C(R$^7$)R$^8$, SR$^7$, S(=O)R$^7$, S(=O)$_2$R$^7$, and C(=NR$^7$)NHR$^8$;

R$^5$ and R$^6$ are independently selected from the group consisting of H, lower alkyl, aralkyl, heterocyclic, and heterocycloalkyl, said lower alkyl, aralkyl, heterocyclic, and heterocycloalkyl groups being optionally substituted with one or more hydroxy, alkoxy, aryloxy, carboxy, alkoxycarbonyl, aryloxycarbonyl, amino, monoalkylamino, dialkylamino, monoarylamino, diarylamino, or halogen groups;

R$^1$, R$^2$, and R$^3$, independently, are selected from the group consisting of H, lower alkyl, aryl, and heterocyclyl, said lower alkyl, aryl and heterocyclyl groups being optionally substituted with one or more J groups;

or R$^2$ and R$^3$, may be taken together with the carbon and nitrogen atoms to which they are attached to form a 4–8 membered ring which is optionally substituted with one or more J groups;

R$^7$ and R$^8$, independently, are selected from the group consisting of H, lower alkyl, aralkyl, heterocyclic, and heterocycloalkyl, said lower alkyl, aralkyl, heterocyclic, and heterocycloalkyl groups being optionally substituted with one or more hydroxy, alkoxy, aryloxy, carboxy, alkoxycarbonyl, aryloxycarbonyl, amino, monoalkylamino, dialkylamino, monoarylamino, diarylamino, or halogen groups;

M is a pharmaceutically acceptable cation selected from the group consisting of sodium, lithium, potassium, calcium, magnesium, zinc, aluminum, ammonium, mono-, di-, tri-, or tetraalkylammonium, morpholinium, piperidinium, and megluminium; and with the proviso that R$^2$ and R$^3$ taken together is other than —CH$_2$—CH$_2$—CH$_2$.

In some preferred embodiments of the compounds of Formula I R$^1$ is lower alkyl or lower alkyl substituted with J.

In some preferred embodiments, J is cycloalkyl, aryl, or aryl substituted with aralkyloxy. In more preferred embodiments, R$^1$ is ethyl, isopropyl, benzyl, isobutyl, cyclohexylmethyl, or 4-benzyloxybenzyl.

In other preferred embodiments, R$^2$ is alkyl or cycloalkyl. In more preferred embodiments, R$^2$ is isobutyl, isopropyl, or cyclopentyl.

In some preferred embodiments, R$^3$ is H. In other preferred embodiments, R$^2$ and R$^3$ are taken together with the carbon and nitrogen atoms to which they are attached to form a 4–8 membered ring which is optionally substituted with one or more J groups.

In some preferred embodiments, G is H or C(=O)NHEt. More preferably, G is H.

In further preferred embodiments, A is alkyl, aryl, aralkyl, or tetrahydroisoquinolin-2-yl. In especially preferred embodiments, A is methyl, tolyl, naphthyl, benzyl, or tetrahydroisoquinolin-2-yl. Most preferably, A is benzyl.

In still other preferred embodiments, B is C(=O), OC(=O), or S(=O)$_2$. In more preferred embodiments, B is C(=O) or OC(=O). In especially preferred embodiments, A is benzyl and B is OC(=O).

In further preferred embodiments, R$^3$ is H, n is 0, 1, or 2, and M is sodium. Most preferably, n is 0.

In still further preferred embodiments, Aaa is independently Ala, Phe, or Leu.

As used herein, the term "alkyl" includes straight-chain, branched and cyclic hydrocarbon groups such as, for example, ethyl, isopropyl and cyclopentyl groups. Preferred alkyl groups have 1 to about 10 carbon atoms. "Cycloalkyl" groups are cyclic alkyl groups. "Aryl" groups are aromatic cyclic compounds including but not limited to phenyl, tolyl, naphthyl, anthracyl, phenanthryl, pyrenyl, and xylyl. Preferred aryl groups include phenyl and naphthyl. The term "carbocyclic", as used herein, refers to cyclic groups in which the ring portion is composed solely of carbon atoms. The term "lower alkyl" refers to alkyl groups of 1 to about 6 carbon atoms. The term "halogen" refers to F, Cl, Br, and I atoms. The term "aralkyl" denotes alkyl groups which bear aryl groups, for example, benzyl groups. As used herein, "alkoxy" groups are alkyl groups linked through an oxygen atom. Examples of alkoxy groups include methoxy (—OCH$_3$) and ethoxy (—OCH$_2$CH$_3$) groups. In general, the term "oxy" when used as a suffix denotes attachment through an oxygen atom. Thus, alkoxycarbonyl groups are carbonyl groups which contain an alkoxy substituent, i.e., groups of general formula —C(=O)—O—R, where R is alkyl. The term "aryloxy" denotes an aryl group linked through an oxygen atom, and the term "aralkyloxy" denotes an aralkyl group linked through an oxygen atom.

The terms "heterocycle", "heterocyclyl", and "heterocyclic" refer to cyclic groups in which a ring portion includes at least one heteroatom such as O, N or S. Heterocyclic groups include "heteroaryl" as well as "heteroalkyl" groups. "Heterocycloalkyl" denotes a heterocycle attached through a lower alkyl group. The term "heteroaryl" denotes aryl groups having one or more hetero atoms contained within an aromatic ring. The term "heteroarylalkyl" denotes a heteroaryl group attached through an alkyl group. The term "heteroalkyl" denotes a heterocyclic group which contains at least one saturated carbon atom in a heterocyclic ring. Examples of heteroalkyl groups include piperidine, dihydropyridine, and tetrahydroisoquinolin-2-yl groups.

As used herein, the term "amino acid" denotes a molecule containing both an amino group and a carboxyl group. As used herein the term "L-amino acid" denotes an α-amino acid having the L- configuration around the α-carbon, that is, a carboxylic acid of general formula CH(COOH) (NH$_2$)-(side chain), having the L-configuration. The term "D-amino acid" similarly denotes a carboxylic acid of general formula CH(COOH) (NH$_2$)-(side chain), having the D-configuration around the α-carbon. Side chains of L-amino acids include naturally occurring and non-naturally occurring moieties. Nonnaturally occurring (i.e., unnatural) amino acid side chains are moieties that are used in place of naturally occurring amino acid sidechains in, for example, amino acid analogs. See, for example, Lehninger, *Biochemistry*, Second Edition, Worth Publishers, Inc, 1975, pages 73–75. One representative amino acid side chain is the lysyl side chain, —(CH$_2$)$_4$—NH$_2$. Other representative α-amino acid side chains are shown below in Table 1.

TABLE 1

CH$_3$—
HO—CH$_2$—
C$_6$H$_5$—CH$_2$—
HO—C$_6$H$_4$—CH$_2$—

TABLE 1-continued

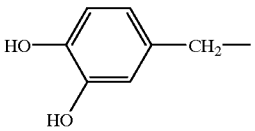

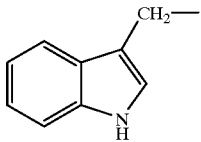

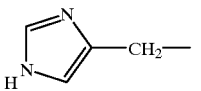

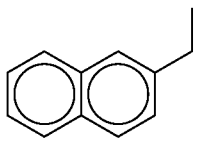

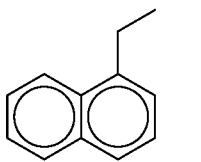

HS—CH$_2$—
HO$_2$C—CH(NH$_2$)—CH$_2$—S—S—CH$_2$—
CH$_3$—CH$_2$—
CH$_3$—S—CH$_2$—CH$_2$—
CH$_3$—CH$_2$—S—CH$_2$—CH$_2$—
HO—CH$_2$—CH$_2$—
CH$_3$—CH(OH)—
HO$_2$C—CH$_2$—NHC(=O)—CH$_2$—

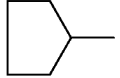

HO$_2$C—CH$_2$—CH$_2$—
NH$_2$C(=O)—CH$_2$—CH$_2$—
(CH$_3$)$_2$—CH—
(CH$_3$)$_2$—CH—CH$_2$—
CH$_3$—CH$_2$—CH$_2$—
H$_2$N—CH$_2$—CH$_2$—CH$_2$—
H$_2$N—C(=NH)—NH—CH$_2$—CH$_2$—CH$_2$—
H$_2$N—C(=O)—NH—CH$_2$—CH$_2$—CH$_2$—
CH$_3$—CH$_2$—CH(CH$_3$)—
CH$_3$—CH$_2$—CH$_2$—CH$_2$—
H$_2$N—CH$_2$—CH$_2$—CH$_2$—CH$_2$—

The amino acid substituents denoted "Aaa" in the compounds of Formula I can be identical to each other, or can be different from each other.

Compounds of Formula I contain a moiety of formula:

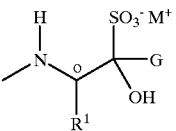

wherein the symbol "o" denotes a carbon atom which can be in either stereochemical configuration (i.e., R or S). Thus, included within the present invention are compounds of Formula I wherein the carbon atom denoted by "o" has the R configuration, compounds of Formula I wherein the carbon atom denoted by "o" has the S configuration, and any mixtures thereof.

Functional groups present in the compounds of Formula I may contain blocking groups. Blocking groups are known per se as chemical functional groups that can be selectively appended to functionalities, such as hydroxyl groups, amino groups, thio groups, and carboxyl groups. Protecting groups are blocking groups which can be readily removed from functionalities. These groups are present in a chemical compound to render such functionality inert to chemical reaction conditions to which the compound is exposed. Any of a variety of protecting groups may be employed with the present invention. Examples of such protecting groups are the benzyloxycarbonyl (Cbz; Z), t-butoxycarbonyl, methyl ester, and benzyl ether groups. Other preferred protecting groups according to the invention may be found in Greene, T. W. and Wuts, P. G. M., *"Protective Groups in Organic Synthesis"* 2d. Ed., Wiley & Sons, 1991.

Further blocking groups useful in the compounds of the present invention include those that bear acyl, aroyl, lower alkyl, alkanesulfonyl, aralkanesulfonyl, or arylsulfonyl substituents on their amino groups.

The peptidyl-2-amino-1-hydroxyalkanesulfonic acids of the invention have the unexpected advantage of excellent solubility in aqueous media, preferably approximately between 1 and 300 mg/mL, and preferably at temperatures between approximately 0° and 40° C., with 25° C. being especially preferred. The compounds of the invention are preferably soluble at concentrations greater than about 5 mg/mL. More preferably, the compounds of the invention are soluble at concentrations above about 20 mg/mL. Thus, the compounds can be easily administered parenterally, for example intravenously, by bolus or infusion in the clinical or laboratory setting in media such as optionally buffered water, aqueous saline, or aqueous saline buffers at approximately pH 5 to 8, preferably pH 6.5 to 7.5. Examples of these media include water, optionally buffered 0.85% (145 mM) sodium chloride, phosphate buffered saline (10 mM phosphate, 120 mM NaCl, 2.7 mM KCl, pH 7.4), and Locke's buffer (10 mM HEPES, 154 mM NaCl, 5.6 mM KCl 2.3 mM CaCl$_2$, 5 uM glycine, 20 mM glucose, 1 mM sodium pyruvate, pH 7.4). The enhanced aqueous solubility of the compounds of the invention is a significant improvement over the solubilities of many other cysteine protease inhibitors. For example, the aqueous solubility of the analogous dipeptide aldehyde and α-ketoamide inhibitors are typically less than 1 mg/mL. See Harbeson et al. *J. Med. Chem.* 1994, 37, 2918–2929.

Because the peptidyl-2-amino-1-hydroxyalkanesulfonic acids of the invention inhibit cysteine proteases, they can be used in both research and therapeutic settings. Inhibition of cysteine protease activity can be measured using compounds of the invention. Thus, in a research environment, preferred compounds having defined attributes can be used to screen for natural and synthetic compounds which evidence similar characteristics in inhibiting protease activity. The compounds of the invention also can be used in the refinement of in vitro and in vivo models for determining the effects of inhibition of particular proteases on particular cell types or biological conditions. In a therapeutic setting, given the connection between cysteine proteases and certain defined disorders, compounds of the invention can be utilized to alleviate, mediate, reduce and/or prevent disorders which are associated with abnormal and/or aberrant activity of cysteine proteases.

In preferred embodiments, compositions are provided for inhibiting a cysteine protease comprising a compound of the invention. In other preferred embodiments, methods are provided for inhibiting cysteine proteases comprising contacting a protease selected from the group consisting of cysteine proteases with an inhibitory amount of a compound of the invention.

The disclosed compounds of the invention are useful for the inhibition of cysteine proteases. As used herein, the terms "inhibit" and "inhibition" mean having an adverse effect on enzymatic activity. An inhibitory amount is an amount of a compound of the invention effective to inhibit a cysteine protease. The term "reversible", when used to modify "inhibit" and "inhibition", means that such adverse effect on catalytic activity can be reversed. The term "irreversible", when used to modify "inhibit" and "inhibition", means that such adverse effect on catalytic activity cannot be reversed.

Compounds provided herein can be formulated into pharmaceutical compositions by admixture with pharmaceutically acceptable nontoxic excipients and carriers. As noted above, such compositions may be prepared for use in parenteral administration, particularly in the form of liquid solutions or suspensions; or oral administration, particularly in the form of tablets or capsules; or intranasally, particularly in the form of powders, nasal drops, or aerosols; or dermally, via, for example, trans-dermal patches; or prepared in other suitable fashions for these and other forms of administration as will be apparent to those skilled in the art.

The composition may conveniently be administered in unit dosage form and may be prepared by any of the methods well known in the pharmaceutical art, for example, as described in *Remington's Pharmaceutical Sciences* (Mack Pub. Co., Easton, Pa., 1980). Formulations for parenteral administration may contain as common excipients sterile water or saline, polyalkylene glycols such as polyethylene glycol, oils and vegetable origin, hydrogenated naphthalenes and the like. In particular, biocompatible, biodegradable lactide polymer, lactide/glycolide copolymer, or polyoxyethylene-polyoxypropylene copolymers may be useful excipients to control the release of the active compounds. Other potentially useful parenteral delivery systems for these active compounds include ethylene-vinyl acetate copolymer particles, osmotic pumps, implantable infusion systems, and liposomes. Formulations for inhalation administration contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally. Formulations for parenteral administration may also include glycocholate for buccal administration, a salicylate for rectal administration, or citric acid for vaginal administration. Formulations for transdermal patches are preferably lipophilic emulsions.

The materials of this invention can be employed as the sole active agent in a pharmaceutical or can be used in combination with other active ingredients. The concentrations of the compounds described herein in a therapeutic composition will vary depending upon a number of factors, including the dosage of the drug to be administered, the chemical characteristics (e.g., hydrophobicity) of the compounds employed, and the route of administration. In general terms, the compounds of this invention may be provided in an aqueous physiological buffer solution containing about 0.1 to 30% w/v compound for parenteral administration. Typical dose ranges are from about 1 µg/kg to about 1 g/kg of body weight per day; a preferred dose range is from about 0.01 mg/kg to 100 mg/kg of body weight per day. The preferred dosage of drug to be administered is likely to depend on such variables as the type and extent of progression of the disease or disorder, the overall health status of the particular patient, the relative biological efficacy of the compound selected, and formulation of the compound excipient, and its route of administration.

As used herein, the term "contacting" means directly or indirectly causing at least two moieties to come into physical association with each other. Contacting thus includes physical acts such as placing a compound of the invention together with a protease in a container, or administering a compound of the invention to a patient. Thus, for example, administering a compound of the invention to a human patient evidencing a disease or disorder associated with abnormal and/or aberrant activity of such proteases falls within the scope of the definition of the term "contacting".

The invention is further illustrated by way of the following examples which are intended to elucidate the invention. These examples are not intended, nor are they to be construed, as limiting the scope of the disclosure.

EXAMPLE 1

Synthesis of Compound I

Benzyloxycarbonyl-L-valyl-2-amino-1-hydroxy-3-phenylpropanesulfonic acid sodium salt A suspension of 198 mg (0.52 mmol) of benzyloxycarbonyl-Val-Phe-H (prepared as described by Angelastro, Mehdi, Burkhart, Peet, and Bey; *J. Med. Chem.* 1990, 33, 13–16) in 4 mL of ethyl acetate was stirred at room temperature as 57.2 mg (0.55 mmol, 1.06 eq.) of sodium bisulfite in 4 mL of water was added dropwise. Then the reaction was stirred vigorously for 2 h. The two layers were separated, and the organic layer was washed with water (3×2 mL). The organic layer was dried over $MgSO_4$ to give 82 mg (41%) of recovered starting material. The combined aqueous layers were filtered, cooled to −78° C. and lyophilized to give 180 mg (66%) of Compound 1 as a white hygroscopic solid.

$^1$H NMR (DMSO-d$_6$) δ0.76 and 0.77 (2d, 6H), 1.88, 2.00(2m, 1H), 2.60, 3.40 (2m, 1H), 2.90 (m, 1H), 3.80–3.90 (m, 3H), 4.15, 4.35(m, 1H), 5.05 (d, 2H), 5.45, 5.70 (2d, 1H), 7.05–7.40(m, 10H), 7.05, 7.90(2d, 1H). ES$^+$ MS m/z 509 (M+Na); ES$^-$ MS m/z 463 (M$^-$).

Anal. Calc'd for C$_{22}$H$_{27}$N$_2$O$_7$SNa·0.65 NaHSO$_3$: C, 47.69; H, 5.03; N, 4.56. Found: C, 47.72; H, 4.51; N, 4.56.

Compounds 2–4 were synthesized by substantially the same procedure as described in Example 1 starting with the corresponding peptide aldehydes.

EXAMPLE 2

Synthesis of Compound 2

Tetrahydroisoquinoline-2-carbonyl-L-leucyl-2-amino-1-hydroxy-3-phenylpropanesulfonic acid sodium salt $^1$H NMR (DMSO-d$_6$) δ0.80(2d, 6H), 1.2–1.7 (m, 3H), 2.3 (m, 2H), 2.6–2.9(m, 3H), 3.5–3.9(m, 4H), 4.1(m, 1H), 5.3 (m, 1H), 5.50.5.70(2d, 1H), 7.2 (m, 9H), 7.5, 7.60 (2d, 1H). ES$^-$ MS m/z 501 (M$^-$).

EXAMPLE 3

Synthesis of Compound 3

Benzyloxycarbonyl-L-cyclopentylglycyl-2-amino-1-hydroxy-3-phenylpropanesulfonic acid sodium salt $^1$H NMR (DMSO-d$_6$) δ1.1–1.6 (m, 8H), 1.95, 2.10 (m, 1H), 2.30–2.60(m, 2H), 2.90 (m, 1H), 3.70, 3.80 (m, 1H), 4.10, 4.30 (m, 1H), 5.0 (d, 2H), 5.50, 5.70 (2d, 1H), 7.1–7.4(m, 10.5 H), 7.80 (d, 0.5H). ES$^+$ MS m/z 535 (M+Na); ES$^-$ MS m/z 489 (M$^-$).

Anal. Calc'd for C$_{24}$H$_{29}$N$_2$O$_7$SNa·6NaHSO$_3$: C, 25.33; H, 3.08; N, 2.46. Found: C, 25.76; H, 2.55; N, 2.26.

EXAMPLE 4

Synthesis of Compound 4

Benzyloxycarbonyl-L-leucyl-2-amino-1-hydroxybutanesulfonic acid sodium salt $^1$H NMR (DMSO-d$_6$) δ0.65–0.9 (m, 9H), 1.4–1.8 (m, 4H), 1.87 (m, 1H), 3.8–4.05(m, 3H), 5.0 (s, 2H), 5.2, 5.5 (2d, 1H), 7.3–7.6 (m, 6H). ES$^+$ MS m/z 461 (M+Na); ES$^-$ MS m/z 415 (M$^-$)

Anal. Calc'd for C$_{18}$H$_{27}$N$_2$O$_7$SNa·0.8 NaHSO$_3$: C, 41.43; H, 5.37; N, 5.37. Found: C, 41.43; H. 5.42; N, 5.13.

Other peptidyl-2-amino-1-hydroxyalkanesulfonic acids of the invention, listed below and shown in Table II, are prepared by substantially the same procedure as described in Example 1 starting with the corresponding peptide aldehydes. Such peptide aldehyde starting materials may be readily obtained from commercial sources, and/or prepared from available starting materials using methodology well known to those skilled in the art. For example, see, M. Iqbal et al., *Bioorg. Med. Chem. Lett.* 1997, 7, 539–544. The compound of Example 16 is prepared starting with the corresponding peptide α-ketoamide which can be prepared by the method of Harbeson et al., *J. Med. Chem.* 1994, 37, 2918–2929.

EXAMPLE 5

Benzyloxycarbonyl-L-t-butylglycyl-2-amino-1-hydroxy-4-methylpentanesulfonic acid sodium salt

EXAMPLE 6

Benzyloxycarbonyl-L-leucyl-2-amino-1-hydroxy-4-methylpentanesulfonic acid sodium salt

EXAMPLE 7

Benzyloxycarbonyl-L-leucyl-2-amino-3-cyclohexyl-1-hydroxy-3-propanesulfonic acid sodium salt

EXAMPLE 8

Benzyloxycarbonyl-L-leucyl-2-amino-1-hydroxy-3-((4-benzyloxy)phenyl)propanesulfonic acid sodium salt

EXAMPLE 9

Benzyloxycarbonyl-L-leucyl-2-amino-1-hydroxy-3-methylbutanesulfonic acid sodium salt

EXAMPLE 10

Toluenesulfonyl-L-leucyl-2-amino-1-hydroxy-4-methylpentanesulfonic acid sodium salt

EXAMPLE 11

Benzyloxycarbonyl-L-alanyl-L-leucyl-2-amino-1-hydroxy-4-methylpentanesulfonic acid sodium salt

EXAMPLE 12

Benzyloxycarbonyl-L-phenylalanyl-L-leucyl-2-amino-1-hydroxy-4-methylpentanesulfonic acid sodium salt

EXAMPLE 13

Naphthyl-2-carbonyl-L-leucyl-L-leucyl-2-amino-1-hydroxy-4-methylpentanesulfonic acid sodium salt

EXAMPLE 14

Methanesulfonyl-L-prolyl-2-amino-1-hydroxy-3-phenylpropanesulfonic acid sodium salt

EXAMPLE 15

Benzyloxycarbonyl-L-alanyl-L-leucyl-L-leucyl-2-amino-1-hydroxy-4-methylpentanesulfonic acid sodium salt

EXAMPLE 16

Benzyloxycarbonyl-L-valyl-2-amino-1-(ethylaminocarbonyl)-1-hydroxy-3-phenylpropanesulfonic acid sodium salt

TABLE II

Peptidyl-2-amino-1-hydroxyalkanesulfonic Acids $$\text{A-B}-(\text{Aaa})_{\overline{n}}-\underset{R^3}{N}-\underset{\underset{O}{\parallel}}{\overset{R^2}{C}}-\underset{R^1}{\overset{H}{N}}-\overset{SO_3^-Na^+}{\underset{OH}{C}}-G$$

| Cmpd | A-B | (Aaa)$_n$ | n | R$^3$ | R$^2$ | R$^1$ | G |
|---|---|---|---|---|---|---|---|
| 5 | PhCH$_2$OCO | — | 0 | H | (CH$_3$)$_3$C | (CH$_3$)$_2$CHCH$_2$ | H |
| 6 | PhCH$_2$OCO | — | 0 | H | (CH$_3$)$_2$CHCH$_2$ | (CH$_3$)$_2$CHCH$_2$ | H |
| 7 | PhCH$_2$OCO | — | 0 | H | (CH$_3$)$_2$CHCH$_2$ | Cyclohexyl CH$_2$ | H |
| 8 | PhCH$_2$OCO | — | 0 | H | (CH$_3$)$_2$CHCH$_2$ | 4-(PhCH$_2$O)-PhCH$_2$ | H |
| 9 | PhCH$_2$OCO | — | 0 | H | (CH$_3$)$_2$CHCH$_2$ | (CH$_3$)$_2$CH | H |
| 10 | Toluene-SO$_2$ | — | 0 | H | (CH$_3$)$_2$CHCH$_2$ | (CH$_3$)$_2$CHCH$_2$ | H |
| 11 | PhCH$_2$OCO | Ala | 1 | H | (CH$_3$)$_2$CHCH$_2$ | (CH$_3$)$_2$CHCH$_2$ | H |
| 12 | PhCH$_2$OCO | Phe | 1 | H | (CH$_3$)$_2$CHCH$_2$ | (CH$_3$)$_2$CHCH$_2$ | H |
| 13 | Naphthyl-2-CO | Leu | 1 | H | (CH$_3$)$_2$CHCH$_2$ | (CH$_3$)$_2$CHCH$_2$ | H |
| 14 | CH$_3$SO$_2$ | — | 0 | —CH$_2$CH$_2$CH$_2$— | | PhCH$_2$ | H |
| 15 | PhCH$_2$OCO | Ala-Leu | 2 | H | (CH$_3$)$_2$CHCH$_2$ | (CH$_3$)$_2$CHCH$_2$ | H |
| 16 | PhCH$_2$OCO | — | 0 | H | (CH$_3$)$_2$CH | PhCH$_2$ | CON-HEt |

Ph = Phenyl

EXAMPLE 17
Inhibition of Cysteine Protease Activity

To evaluate inhibitory activity, stock solutions (40 concentrated) of each compound to be tested were prepared in 100% anhydrous DMSO and 5 μl of each inhibitor preparation were aliquoted into each of three wells of a 96-well plate. Recombinant human calpain I, prepared by the of Meyer et al. (*Biochem. J.* 1996, 314: 511–519), was diluted into assay buffer (i.e., 50 mM Tris, 50 mM NaCl, 1 mM EDTA, 1 mM EGTA, and 5mM β-mercaptoethanol, pH 7.5, including 0.2 mM Succ-Leu-Tyr-MNA), and 175 μl was aliquoted into the same wells containing the independent inhibitor stocks as well as to positive control wells which contained 5 μl DMSO, but no compound. To start the reaction, 20 μl of 50 mM CaCl$_2$ in assay buffer was added to all wells of the plate, excepting three, which were used as background signal baseline controls. Substrate hydrolysis was monitored every 5 minutes for a total of 30 minutes. Substrate hydrolysis in the absence of inhibitor was linear for up to 15 minutes.

Inhibition of calpain I activity was calculated as the percent decrease in the rate of substrate hydrolysis in the presence of inhibitor relative to the rate in its absence. Comparison between the inhibited and control rates was made within the linear range for substrate hydrolysis. The IC$_{50}$ values for inhibitors (concentration yielding 50% inhibition) were determined from the percent decrease in rates of substrate hydrolysis in the presence of five to seven different concentrations of the test compound. The results were plotted as percent inhibition versus log inhibitor concentration, and the IC$_{50}$ was calculated by fitting the data to the four-parameter logistic equation shown below using the program GraphPad Prism (GraphPad Software, Inc., San Diego, Calif.).

$$y = d + [(a-d)/(1+(x/c)^b)]$$

In the equation above, the parameters a, b, c, and d are defined as follows: a is % inhibition in the absence of inhibitor, b is the slope, c is the IC$_{50}$, and d is the % inhibition at an infinite concentration of inhibitor.

Results are presented in Table III.

TABLE III

Inhibition of Calpain I by Peptidyl-2-amino-1-hydroxyalkanesulfonic Acids $$\text{A-B}-(\text{Aaa})_{\overline{n}}-\underset{R^3}{N}-\underset{\underset{O}{\parallel}}{\overset{R^2}{C}}-\underset{R^1}{\overset{H}{N}}-\overset{SO_3^-Na^+}{\underset{OH}{C}}-G$$

| Cmpd | A-B | (Aaa)$_n$ | n | R$^3$ | R$^2$ | R$^1$ | G | IC$_{50}$ (nM) |
|---|---|---|---|---|---|---|---|---|
| 1 | PhCH$_2$OCO | — | 0 | H | (CH$_3$)$_2$CH | PhCH$_2$ | H | 10 |
| 2 | THIQ-2-CO | — | 0 | H | (CH$_3$)$_2$CHCH$_2$ | PhCH$_2$ | H | 32 |

TABLE III-continued

Inhibition of Calpain I by Peptidyl-2-amino-1-hydroxyalkanesulfonic Acids

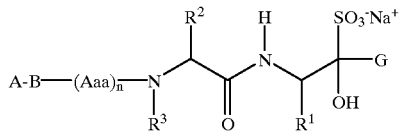

| Cmpd | A-B | (Aaa)$_n$ | n | R$^3$ | R$^2$ | R$^1$ | G | IC$_{50}$ (nM) |
|---|---|---|---|---|---|---|---|---|
| 3 | PhCH$_2$OCO | — | 0 | H | Cyclopentyl | PhCH$_2$ | H | 15 |
| 4 | PhCH$_2$OCO | — | 0 | H | (CH$_3$)$_2$CHCH$_2$ | CH$_2$CH$_3$ | H | 20 |

Ph = Phenyl; THIQ = tetrahydroisoquinolin-2-yl

EXAMPLE 18

Solubility of Inhibitors

To determine the solubility of peptidyl-2-amino-1-hydroxyalkanesulfonic acid inhibitors, Locke's buffer (10 mM HEPES, 154 mM NaCl, 5.6 mM KCl, 2.3 mM CaCl$_2$, 5 uM glycine, 20 mM glucose, 1 mM sodium pyruvate, pH 7.4) was added slowly to a weighed sample of the peptidyl-2-amino-1-hydroxyalkanesulfonic acid in a sonicator at 20° C. until all of the solid was dissolved. Solubilities of the control peptide aldehyde inhibitors, generally insufficient to be accurately determined by this method, were determined by UV absorption as follows: The inhibitor (1 mg) was dissolved in DMSO (10 μL), the solution was diluted with Locke's buffer (2 mL), sonicated for 5 min, and filtered to remove the excess undissolved inhibitor. The UV absorbance of the inhibitor dissolved in the filtrate was measured, generally from 220–340 nm, and the concentration was calculated by comparison with a known concentration of the inhibitor dissolved in methanol (generally 0.5 mg/mL). Comparison of the solubilities of the compounds of the invention with related aldehydes is shown in Table IV.

TABLE IV

Solubility Comparisons

| | Solubility (mg/mL) |
|---|---|
| Compound of Invention | |
| Cbz-Val-NHCH(Bn)CH(OH)SO$_3$Na (1) | 8.2 |
| THIQ-2-CO-Leu-NHCH(Bn)CH(OH)SO$_3$Na (2) | 37 |
| Cbz-CyclopentylGly-NHCH(Bn)CH(OH)SO$_3$Na (3) | 27 |
| Cbz-Leu-NHCH(CH$_2$CH$_3$)CH(OH)SO$_3$Na (4) | 93 |
| Control Compound | |
| Cbz-Val-Phe-H | 0.18 |
| THIQ-2-CO-Leu-Phe-H | 0.18 |
| Cbz-CyclopentylGly-Phe-H | 0.08 |
| Cbz-Leu-Abu-H | 0.21 |

It is intended that each of the patents, applications, and printed publications mentioned in this patent document be hereby incorporated by reference in their entirety.

As those skilled in the art will appreciate, numerous changes and modifications may be made to the preferred embodiments of the invention without departing from the spirit of the invention. It is intended that all such variations fall within the scope of the invention.

What is claimed is:

1. A compound of the Formula:

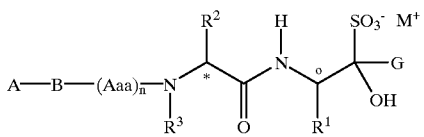

wherein:
* denotes the α-carbon of an α-amino acid residue having the L configuration;
o denotes a carbon having either stereochemical configuration, or a mixture thereof;
A is selected from the group consisting of lower alkyl, aryl having from 6 to about 14 carbons, heterocyclyl having from about 5 to about 14 ring atoms, heterocycloalkyl having from about 5 to about 14 ring atoms, aralkyl having from about 7 to about 15 carbons, and heteroarylalkyl, said alkyl, aryl, heterocyclyl, heterocycloalkyl, aralkyl and heteroarylalkyl groups being optionally substituted with J;
B is selected from the group consisting of C(=O), OC(=O), S(=O), S(=O)$_2$, and NR$^4$C(=O), where R$^4$ is H or lower alkyl;
each Aaa is independently an amino acid which optionally contains one or more blocking groups;
n is 0, 1, 2, or 3;
G is selected from the group consisting of H, C(=O) NR$^5$R$^6$, C(=O)OR$^5$, CF$_3$, CF$_2$R$^5$, P(=O) (R$^5$) (OR$^6$) and P(=O) (OR$^5$) (OR$^6$);
J is selected from the group consisting of halogen, lower alkyl, cycloalkyl, aryl, heteroaryl, heterocycloalkyl, aryl substituted with aralkyloxy, C(=O)OR$^7$, OC(=O) R$^7$, NR$^8$C(=O)OR$^7$, OR$^7$, CN, NO$_2$, N=C(R$^7$)R$^8$, SR$^7$, S(=O)R$^7$, S(=O)$_2$R$^7$, and C(=NR$^7$) NHR$^8$;
R$^5$ and R$^6$ are independently selected from the group consisting of H, lower alkyl, aralkyl, heterocyclic, and heterocycloalkyl, said lower alkyl, aralkyl, heterocyclic, and heterocycloalkyl groups being optionally substituted with one or more hydroxy, alkoxy, aryloxy, carboxy, alkoxycarbonyl, aryloxycarbonyl, amino, monoalkylamino, dialkylamino, monoarylamino, diarylamino, or halogen groups;
R$^1$, R$^2$, and R$^3$, independently, are selected from the group consisting of H, lower alkyl, aryl, and heterocyclyl, said lower alkyl, aryl and heterocyclyl groups being optionally substituted with one or more J groups;

or $R^2$ and $R^3$, may be taken together with the carbon and nitrogen atoms to which they are attached to form a 4–8 membered ring which is optionally substituted with one or more J groups;

$R^7$ and $R^8$, independently, are selected from the group consisting of H, lower alkyl, aralkyl, heterocyclic, and heterocycloalkyl, said lower alkyl, aralkyl, heterocyclic, and heterocycloalkyl groups being optionally substituted with one or more hydroxy, alkoxy, aryloxy, carboxy, alkoxycarbonyl, aryloxycarbonyl, amino, monoalkylamino, dialkylamino, monoarylamino, diarylamino, or halogen groups;

M is a pharmaceutically acceptable cation selected from the group consisting of sodium, lithium, potassium, calcium, magnesium, zinc, aluminum, ammonium, mono-, di-, tri-, or tetraalkylammonium, morpholinium, piperidinium, and megluminium; and with the proviso that $R^2$ and $R^3$ taken together is other than —CH$_2$—$_2$—CH$_2$—.

2. The compound of claim 1 wherein $R^1$ is lower alkyl or lower alkyl substituted with J.

3. The compound of claim 2 wherein $R^1$ is lower alkyl substituted with J, where said J is cycloalkyl, aryl, or aryl substituted with aralkyloxy.

4. The compound of claim 2 wherein $R^1$ is ethyl, isopropyl, benzyl, isobutyl, cyclohexylmethyl, or 4-benzyloxybenzyl.

5. The compound of claim 1 wherein $R^2$ is alkyl or cycloalkyl.

6. The compound of claim 5 wherein $R^2$ is isobutyl, isopropyl, cyclopentyl.

7. The compound of claim 1 wherein $R^3$ is H.

8. The compound of claim 1 wherein $R^2$ and $R^3$ are taken together with the carbon and nitrogen atoms to which they are attached to form a 4–8 membered ring which is not substituted with one or more J groups.

9. The compound of claim 1 wherein $R^2$ and $R^3$ are taken together with the carbon and nitrogen atoms to which they are attached to form a 4–8 membered ring which is substituted with one or more J groups.

10. The compound of claim 1 wherein G is H or C(=O)NHEt.

11. The compound of claim 10 wherein G is H.

12. The compound of claim 1 wherein B is C(=O), OC(=O), or S(=O)$_2$.

13. The compound of claim 12 wherein B is OC(=O) or C(=O).

14. The compound of claim 13 wherein B is OC(=O).

15. The compound of claim 14 wherein A is benzyl.

16. The compound of claim 1 wherein n is 0.

17. The compound of claim 1 where n is 1.

18. The compound of claim 1 wherein n is 2.

19. The compound of claim 1 wherein A is alkyl, aryl, aralkyl, or tetrahydroisoquinolin-2-yl.

20. The compound of claim 1 wherein A is benzyl, methyl, 2-naphthyl or tolyl.

21. The compound of claim 20 wherein A is benzyl.

22. The compound of claim 1 wherein $R^3$ is H, n is 0, 1, or 2, an M is sodium.

23. The compound of claim 22 wherein n is 0.

24. The compound of claim 1 wherein Aaa is independently Ala, Phe, or Leu.

25. The compound of claim 1 wherein the carbon denoted o has the L configuration.

26. The compound of claim 1 wherein the carbon denoted o has the D configuration.

27. The compound of claim 1 wherein the carbon denoted o is racemic.

28. The compound of claim 1 wherein A—B, (Aaa), n, $R^3$, $R^2$, $R^1$ and G are selected in accordance with the following table:

| A-B | (Aaa)$_n$ | n | $R^3$ | $R^2$ | $R^1$ | G |
|---|---|---|---|---|---|---|
| PhCH$_2$OCO | — | 0 | H | (CH$_3$)$_2$CH | PhCH$_2$ | H |
| THIQ-2-CO | — | 0 | H | (CH$_3$)$_2$CHCH$_2$ | PhCH$_2$ | H |
| PhCH$_2$OCO | — | 0 | H | Cyclopentyl | PhCH$_2$ | H |
| PhCH$_2$OCO | — | 0 | H | (CH$_3$)$_2$CHCH$_2$ | CH$_2$CH$_3$ | H |
| PhCH$_2$OCO | — | 0 | H | (CH$_3$)$_3$C | (CH$_3$)$_2$CHCH$_2$ | H |
| PhCH$_2$OCO | — | 0 | H | (CH$_3$)$_2$CHCH$_2$ | (CH$_3$)$_2$CHCH$_2$ | H |
| PhCH$_2$OCO | — | 0 | H | (CH$_3$)$_2$CHCH$_2$ | CyclohexylCH$_2$ | H |
| PhCH$_2$OCO | — | 0 | H | (CH$_3$)$_2$CHCH$_2$ | 4-(PhCH$_2$O)—PhCH$_2$ | H |
| PhCH$_2$OCO | — | 0 | H | (CH$_3$)$_2$CHCH$_2$ | (CH$_3$)$_2$CH | H |
| Toluene-SO$_2$ | — | 0 | H | (CH$_3$)$_2$CHCH$_2$ | (CH$_3$)$_2$CHCH$_2$ | H |
| PhCH$_2$OCO | Ala | 1 | H | (CH$_3$)$_2$CHCH$_2$ | (CH$_3$)$_2$CHCH$_2$ | H |
| PhCH$_2$OCO | Phe | 1 | H | (CH$_3$)$_2$CHCH$_2$ | (CH$_3$)$_2$CHCH$_2$ | H |
| Naphthyl-2-CO | Leu | 1 | H | (CH$_3$)$_2$CHCH$_2$ | (CH$_3$)$_2$CHCH$_2$ | H |
| PhCH$_2$OCO | Ala-Leu | 2 | H | (CH$_3$)$_2$CHCH$_2$ | (CH$_3$)$_2$CHCH$_2$ | H |
| PhCH$_2$OCO | — | 0 | H | (CH$_3$)$_2$CH | PhCH$_2$ | CON—HEt | where Ph is phenyl and THIQ is tetrahydroisoquinolin-2-yl.

29. A composition for inhibiting a protease selected from the group consisting of serine proteases and cysteine proteases comprising a compound of claim 1.

30. A composition for inhibiting a protease selected from the group consisting of serine proteases and cysteine proteases consisting essentially of a compound of claim 1.

31. A method for inhibiting a protease comprising contacting a protease selected from the group consisting of serine proteases and cysteine proteases with an inhibitory amount of a compound of claim 1.

32. A method for inhibiting a protease comprising contacting a protease selected from the group consisting of serine proteases and cysteine proteases with an inhibitory amount of a composition comprising a compound of claim 1.

33. A method for inhibiting a protease comprising contacting a protease selected from the group consisting of serine proteases and cysteine proteases with an inhibitory amount of a composition consisting essentially of a compound of claim 1.

* * * * *

UNITED STATES PATENT AND TRADEMARK OFFICE
CERTIFICATE OF CORRECTION

PATENT NO. : 6,348,448 B1
DATED : February 19, 2002
INVENTOR(S) : Tao et al.

It is certified that error appears in the above-identified patent and that said Letters Patent is hereby corrected as shown below:

Title page,
Item [56], References Cited, OTHER PUBLICATIONS,
"Green, Lawrence R.," reference, please delete "J. org Chem." and insert -- J. Org. Chem. -- therefor.
"Kokeoh, Fritag," reference, please delete "Kokeok, Fritag C." and insert -- Kokesh, Fritz C. -- therefor.
"Lores, Agvin M.," reference, please delete "Agvin" and insert -- Aguin -- therefor.
"Thompson, R.C.," reference, please delete "Serince" and insert -- Serine -- therefor.

Column 11,
Line 33, please insert -- times -- before "concentrated)".
Line 37, please insert -- method -- after "the" and before "of", Column 15,
Line 24, please delete "–$CH_2$–$_2$–$CH_2$–" and insert -- –$CH_2$–$CH_2$–$CH_2$– -- therefor.

Column 16,
Line 20, please delete "or 2, an M is sodium." and insert -- or 2, and M is sodium. -- therefor.

Signed and Sealed this

Fourth Day of January, 2005

JON W. DUDAS
*Director of the United States Patent and Trademark Office*